US008951222B2

(12) United States Patent
Tarlian, Jr. et al.

(10) Patent No.: US 8,951,222 B2
(45) Date of Patent: Feb. 10, 2015

(54) ARTERIAL SHUNT

(75) Inventors: Henry Samuel Tarlian, Jr., Scottsdale, AZ (US); Mitar Vranic, Scottsdale, AZ (US)

(73) Assignee: Western Vascular Institute, Mesa, AZ (US)

(*) Notice: Subject to any disclaimer, the term of this patent is extended or adjusted under 35 U.S.C. 154(b) by 0 days.

(21) Appl. No.: 13/207,241

(22) Filed: Aug. 10, 2011

(65) Prior Publication Data

US 2013/0041305 A1 Feb. 14, 2013

(51) Int. Cl.
*A61M 5/00* (2006.01)
*A61M 1/36* (2006.01)

(52) U.S. Cl.
CPC ........... *A61M 1/3653* (2013.01); *A61M 1/3655* (2013.01)
USPC ............................................................ 604/8

(58) Field of Classification Search
CPC .............................. A61M 1/3655; A61B 17/11
USPC ............................................................ 604/8
See application file for complete search history.

(56) References Cited

U.S. PATENT DOCUMENTS

| | | | | |
|---|---|---|---|---|
| 2,867,213 A * | 1/1959 | Thomas, Jr. | ................ | 604/247 |
| 3,185,128 A * | 5/1965 | Moore et al. | ................ | 562/9 |
| 4,101,874 A * | 7/1978 | Denison et al. | ............ | 340/606 |
| 4,559,034 A * | 12/1985 | Kirita et al. | ............ | 604/522 |
| 4,712,551 A * | 12/1987 | Rayhanabad | ................ | 604/8 |
| 4,731,055 A * | 3/1988 | Melinyshyn et al. | .... | 604/100.02 |
| 4,745,877 A * | 5/1988 | Chang | ................ | 116/274 |
| 4,793,190 A * | 12/1988 | Chang | ................ | 73/861.33 |
| 5,374,239 A * | 12/1994 | Mischenko | ................ | 604/8 |
| 5,876,367 A * | 3/1999 | Kaganov et al. | ............ | 604/8 |
| 6,161,547 A * | 12/2000 | Barbut | ................ | 128/898 |
| 6,436,089 B1 * | 8/2002 | Danielson et al. | ............ | 604/523 |
| 7,087,034 B2 * | 8/2006 | McPherson et al. | ............ | 604/8 |
| 7,144,365 B2 * | 12/2006 | Bolling et al. | ................ | 600/16 |
| 7,445,592 B2 * | 11/2008 | Pecor | ................ | 600/16 |
| 7,458,929 B2 * | 12/2008 | Bolling et al. | ................ | 600/16 |
| 7,513,863 B2 * | 4/2009 | Bolling et al. | ................ | 600/16 |
| 7,537,599 B2 * | 5/2009 | Buelna et al. | ................ | 606/153 |
| 7,588,531 B2 * | 9/2009 | Bolling | ................ | 600/16 |
| 7,614,997 B2 * | 11/2009 | Bolling | ................ | 600/16 |
| 2002/0128679 A1 * | 9/2002 | Turovskiy et al. | ............ | 606/200 |
| 2009/0018172 A1 * | 1/2009 | Dahl et al. | ................ | 514/364 |
| 2009/0018455 A1 | 1/2009 | Chang | | |
| 2009/0024072 A1 * | 1/2009 | Criado et al. | ................ | 604/9 |
| 2009/0198172 A1 | 8/2009 | Garrison et al. | | |
| 2009/0254166 A1 * | 10/2009 | Chou et al. | ................ | 623/1.11 |
| 2010/0160896 A1 * | 6/2010 | Humphrey et al. | ............ | 604/508 |

(Continued)

OTHER PUBLICATIONS

David G. Piepgras: "Clinical and Laboratory Experience with Herpari-Impregnated Silicone Shunts for Carotid Endarterectomy," Ann. Surg. Nov. 1976; pp. 637-641.

*Primary Examiner* — Tatyana Zalukaeva
*Assistant Examiner* — Guy K Townsend
(74) *Attorney, Agent, or Firm* — Sheppard Mullin Richter & Hampton LLP

(57) ABSTRACT

Various embodiments of the present invention are directed toward an arterial shunts for use during vascular surgery. Some embodiments are useful during an endarterectomy, and may be configured for use with specific arteries (e.g., carotid). Additional embodiments may be configured with a filter to prevent clots or plaque from traveling through the shunt, and with a flow meter to provide indication of how much or how little blood is actually passing through the shunt.

19 Claims, 2 Drawing Sheets

(56) References Cited

U.S. PATENT DOCUMENTS

| | | | |
|---|---|---|---|
| 2010/0217276 A1* | 8/2010 | Garrison et al. | 606/128 |
| 2010/0280431 A1* | 11/2010 | Criado et al. | 604/9 |
| 2011/0004147 A1* | 1/2011 | Renati et al. | 604/9 |
| 2011/0034986 A1* | 2/2011 | Chou et al. | 623/1.11 |
| 2011/0087147 A1* | 4/2011 | Garrison et al. | 604/8 |
| 2011/0166496 A1* | 7/2011 | Criado et al. | 604/9 |
| 2011/0166497 A1* | 7/2011 | Criado et al. | 604/9 |

* cited by examiner

ARTERIAL SHUNT

FIELD OF THE INVENTION

The present invention relates to medical devices and, more particularly, some embodiments relate to medical devices used during arterial surgery (e.g., carotid endarterectomy) or peripheral bypass surgery.

DESCRIPTION OF THE RELATED ART

In vascular surgery, it sometimes becomes necessary to perform an endarterectomy to remove blockage lining a constricted artery. Generally, an endarterectomy involves making an incision into an artery where the blockage is present, and removing the obstruction through the incision. In order to facilitate the endarterectomy while still maintaining blood flow through the area, the procedure usually utilizes a shunt that temporarily bypasses (i.e., re-routes) the blood around incision area. In the case of a carotid endarterectomy, a carotid shunt is utilized during the procedure.

The carotid artery is an artery on each side of the neck that supplies blood to the head and neck of the human body. Over time, this artery can become narrowed (carotid stenosis) with the build-up of fatty material (plaque) such as cholesterol. Sometimes, to restore blood flow to the brain and reduce the chances of stroke, a carotid endarterectomy is performed on the carotid artery in order to remove deposits from the blood vessel. The carotid shunt used during the procedure temporarily bypasses blood around the incision area made in the carotid artery, and reduces the length of time that blood flow to the brain is interrupted.

BRIEF SUMMARY OF EMBODIMENTS OF THE INVENTION

Various embodiments of the present invention provide an arterial shunt for use during vascular surgery. In some such embodiments, the arterial shunt is useful during an endarterectomy, and may be configured for use with specific arteries (e.g., carotid). Additional embodiments may be configured with a filter to prevent clots or plaque from traveling through the shunt, and with a flow meter to provide an indication of how much blood is actually passing through the shunt.

According to one embodiment of the invention, a medical shunt is provided, comprising: (i) a first tubular element having a first connection end and an input end; (ii) a second tubular element having a second connection end and an output end, the second connection end being connected to the first connection end such that the second tubular element and the first tubular element are in fluid communication; (iii) a filter disposed within the shunt such that the filter removes impurities from fluid flowing from the input end to the output end; (iv) a flow sensor disposed within the first, second, or third tubular element; (v) a first balloon element disposed on the first tubular element toward the input end; (vi) a second balloon element disposed on the second tubular element toward the output end; (vii) a third tubular element having a third connection end and a distal end, the third connection end connected to the first and second connection ends such that the third tubular element is in fluid communication with the first and second tubular elements; and (viii) a housing connected at the distal end of the third tubular element. In such an embodiment, the housing may comprise a flush port in fluid communication with the first and second tubular elements, a flow meter in electrical communication with the flow sensor, and a balloon inflation port in fluid communication with at least one of the first balloon element or the second balloon element. Throughout this application, it should be well appreciated by those of ordinary skill in the medical device arts that those elements described as being in fluid communication are capable of communicating fluid or gas.

Another embodiment of the invention is directed toward a medical shunt, comprising: (i) a first tubular element having a first connection end and an input end; (ii) a second tubular element having a second connection end and an output end, the second connection end being connected to the first connection end such that the second tubular element and the first tubular element are in fluid communication; (iii) an inline filter disposed within the shunt such that the filter removes impurities from fluid flowing from the input end to the output end; (iv) a flow sensor disposed within the first, second, or third tubular element; (v) a first balloon element disposed on the first tubular element near the input end; (vi) a second balloon element disposed on the second tubular element near the output end; (vii) a third tubular element having a third connection end and a distal end, the third connection end connected to the first and second connection ends such that the third tubular element is in fluid communication with the first and second tubular elements; and (viii) a housing connected at the distal end of the third tubular element. In such an embodiment, the housing may comprise a flush port in fluid communication with the first and second tubular elements, a flow meter comprising a digital optical or audible flow indicator in electrical communication with the flow sensor, a balloon inflation port in fluid communication with at least one of the first balloon element or the second balloon element, a port for administering medication through the shunt or an angiogram port, and a second balloon inflation port, the second balloon inflation port being in fluid communication with the second balloon element and the balloon inflation port being in fluid communication with the first balloon element.

In some embodiments, the housing of the shunt further comprises a port for administering medication through the shunt. In other embodiments, the housing of the shunt further comprises a second balloon inflation port, the second balloon inflation port being in gaseous communication with the second balloon element and the balloon inflation port being in gaseous communication with the first balloon element.

With respect to blood flow, the flow meter in various embodiments comprises an optical or audible flow indicator. For example, the optical or audible flow indicator may be a color gauge that displays specific colors when the blood flow meets specific thresholds. In other examples, the optical flow indicator may be an analog or digital gauge that displays the actual flow measurement in set units (e.g., ml/min). In some embodiments, the flow meter comprises a digital flow meter, which may additionally comprise a digital display indicating a blood flow measurement. In additional embodiments, the flow meter comprises an auditory module, which may output information relating to the blood flow between the input and output ends, or emit an audible signal when blood flow between the input and output ends is occluded. In further embodiments, the auditory module is disposed within the housing of the shunt.

For various embodiments, the filter may be a heparin-bonded filter, which may be capable of filtering various impurities (e.g., plaque, clots, etc.) that could flow from the input end to the output end. The filter in some embodiments may be disposed inline within the first and second tubular elements, and may be located where the first, second, and third connection ends of the first, second, and third tubular elements, respectively, meet.

With respect to the size of the tubular elements, in some embodiments, the second tubular element has a smaller gauge than the first tubular element. For example, an embodiment may comprise a first tubular element having a gauge of 9 French (Fr) or 11 French (Fr), and a second tubular element having a gauge of 9 French. Additionally, in some embodiments, the input end and the output end of the embodiment may be rounded to assist in the insertion of the first and second tubular elements into an artery without traumatizing the artery.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present invention is generally directed toward arterial shunts, which may be used during an endarterectomy (e.g., carotid endarterectomy) to bypass blood around an incision point in the artery. The arterial shunts in accordance with an embodiment may be configured with an inline filter to prevent clots or plaque from traveling through the shunt, and with a flow meter to provide an indication of how much blood is actually passing through the shunt.

Figure 1:
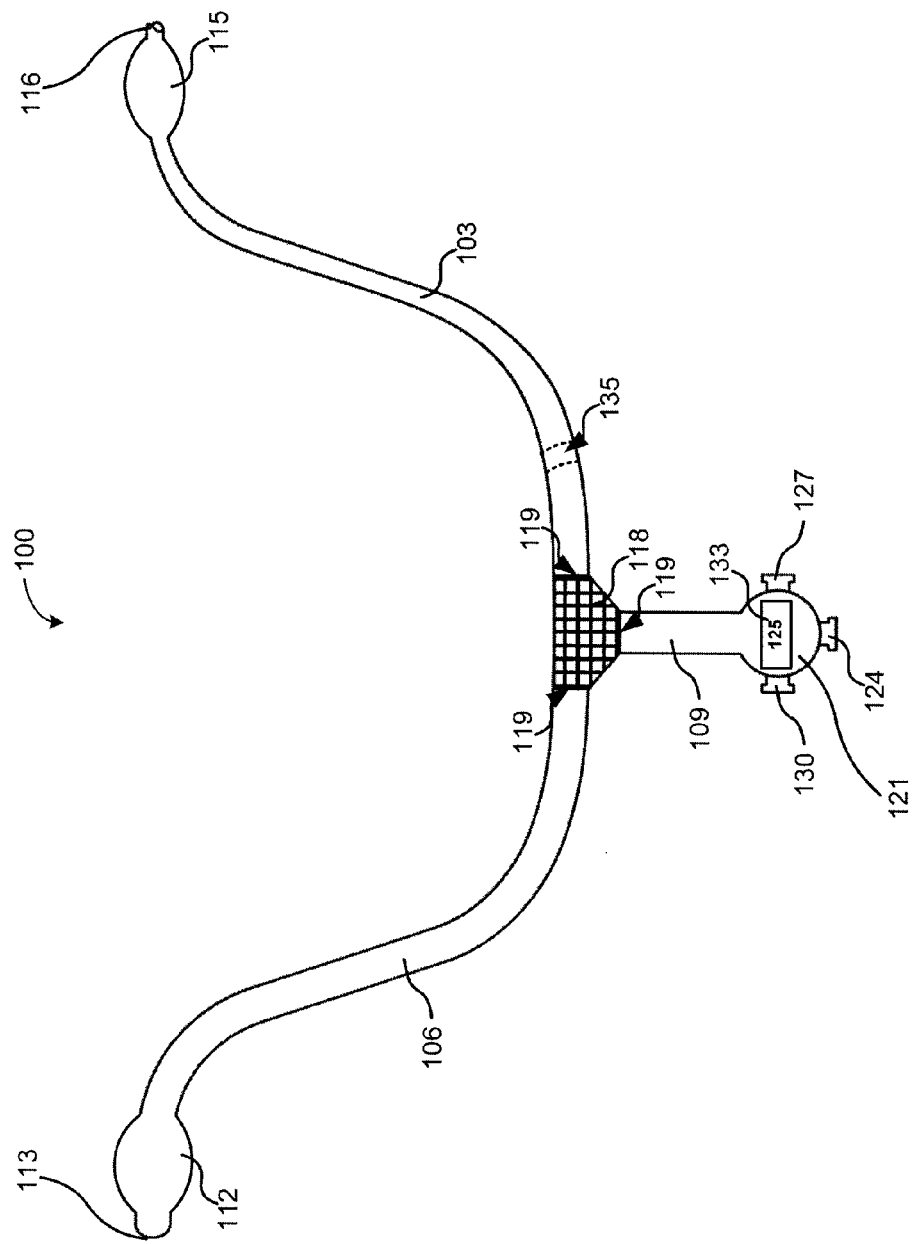
FIG. 1 is a diagram illustrating an example arterial shunt in accordance with one embodiment of the invention.

FIG. 1 is a diagram illustrating an example arterial shunt 100 in accordance with one embodiment of the present invention. Shunt 100 includes a first tubular element 106 and a second tubular element 103, which together function as an arterial lumen to bypass blood around an incision point in an artery, and a third tubular element 109 connected to a housing 121 that comprises several features that will be discussed hereinbelow. Materials from which the tubular elements can be manufactured include silicon and other suitable materials.

As illustrated, the first, second and third tubular elements (106, 103, and 109, respectively) intersect one another at a juncture point (i.e., at inline filter 118) such that the three tubular elements are in fluid communication. In the illustrated embodiment, the first tubular element 106 has a equal or larger gauge than the second tubular element 103. In some embodiments, the gauge of the first tubular element 106 is 11 French, while the gauge of the second tubular element 103 is 9 French. In other embodiments, the first and second tubular elements 106, 103 are the same gauge (e.g., 9 Fr). In some cases, the gauge of the first and second tubular elements may be based variables such as the patient's size, or on the artery with which the shunt is utilized.

In the illustrated embodiment, the first tubular element 106 comprises the input end 113 of the shunt, the second tubular element 103 comprises the output end 116 of the shunt, and both the input and output ends are configured to be inserted into an artery through an incision point. In some embodiments, the input and output ends 113, 116, respectively, may be rounded or tapered to assist in their insertion into an artery. Further details regarding the use of shunt 100 will be provided below when describing FIG. 2, which illustrates a shunt 100 in use with an artery.

Continuing with reference to FIG. 1, configured at the juncture point is an inline filter 118 that is fully contained within the shunt 100. The inline filter 118 may be contained in and protected by a hard or rigid housing. Although this particular filter 118 is positioned at the juncture point of the tubular elements, it should be understood that the inline filter 118 may be positioned elsewhere within the shunt without departing from the scope of the invention. For example, the filter 118 may be placed entirely within the first tubular element 106 before the first, second and third tubular elements intersect, entirely within the second tubular element 103 after the first, second and third tubular element intersect, or located at the main flow ports 119. Regardless of its position, the inline filter 118 functions to filter impurities of blood flowing from the input end 113 to the output end 116. Such blood impurities may include clots (e.g., embolism) and plaque (e.g., from cholesterol build-up). To that end, in some embodiments, the filter 118 is a heparin-bonded filter configured to specifically filter such impurities. Since the filter 118 is disposed inline (i.e., inside of the tubing), no additional steps are required for its deployment. The positioning of the filter 118 within the tubing also protects the filter from contact from the arterial wall, thereby preventing any potential trauma to the arterial wall.

Referring now to the input end 113 and the output end 116, in close proximity to the two ends are balloon elements 112 and 115, respectively, each of which are inflated (either individually or simultaneously) once their respective ends are inserted into an artery. Balloon elements 112 and 115 as shown in FIG. 1 are deflated. Once inserted into the artery and inflated, the balloon elements 112, 115 secure their respective ends 113, 116 within the artery with little to no trauma inflicted on the arterial wall. It will be well understood to one of ordinary skill in the medical device arts that, depending on the embodiment, a balloon element may be inflated either by gas (e.g., air) or fluid (e.g., water). Depending on the embodiment, the balloon elements, like the tubular elements, may be made of silicon.

With further reference to FIG. 1, the housing 121 contains several additional features of the shunt 100, including a port 124 used as a flush port or an angiogram port, two balloon inflation ports (127, 130), and a flow meter 133. In general, the flow meter, with or without the auditory module, provides a surgeon with all the information needed to be sure that the shunt is operating effectively and as designed. In the illustrated shunt 100, the flow meter 133 includes a flow sensor 135 that detects blood flow from the input end 113 to the output end 116, and a digital display 133 that provides blood flow information from the flow sensor 135. For easy readability, the flow meter 133 may be two-sided (i.e., meter display on both sides of housing 121). Depending on the embodiment, the flow sensor 135 may be disposed within the first tubular element 106, the second tubular element 103 (as depicted), the third tubular element 109, or the housing 121. In the illustrated embodiment, the flow meter 133 comprises a digital flow meter, which additionally comprise a digital display indicating a blood flow measurement. As noted before, in other embodiments, the flow meter may comprise an optical flow indicator. For example, the optical flow indicator may be a color gauge that displays specific colors when the blood flow meets specific thresholds. In other examples, the optical flow indicator may be an analog or digital gauge that displays the actual flow measurement in set units (e.g., ml/min). Depending on the embodiment, the shunt 100 may be self-powered (e.g., battery powered) or self-powered from blood flow.

In further embodiments, the flow meter may also comprise an auditory module, which can output information relating to the blood flow between the input and output ends, or emit an audible signal when blood flow between the input and output ends is occluded. For example, if the device detects a thrombosis, an audible signal would be emitted that immediately indicates occlusion of flow. In some embodiments, the auditory module may be completely self-contained within the shunt and, more specifically, may be self-contained within the housing 121. In some embodiments, the housing 121 is waterproof or water-resistant. Additionally, in further embodiments, the audio signal is generated from the unit itself, and the auditory module does not require any extrinsic wires to be placed off the field or connected to an external box for signal generation.

In embodiments where port 124 is an angiogram port, port 124 may be utilized to administer medication to a patient. Where port 124 is a flush port, port 124 may be used to irrigate the various tubular elements of the shunt 100 and may, in some embodiments, also be utilized to administer medication to the patient as well. In other embodiments, a separate port may be provided for administering the medication to a patient. Regardless, in order to achieve its function, the port 124 is in fluid communication with at least one of the tubular elements 106, 103, 109. The balloon inflation ports 127 and 130 are in gaseous or fluid communication with their respective balloon elements 112 and 115, and may be used to either inflate or deflate their respective balloon elements. Additionally, in some embodiments, inflation ports 127 and/or 130 may be configured to operate with a twist-off syringe.

Figure 2:
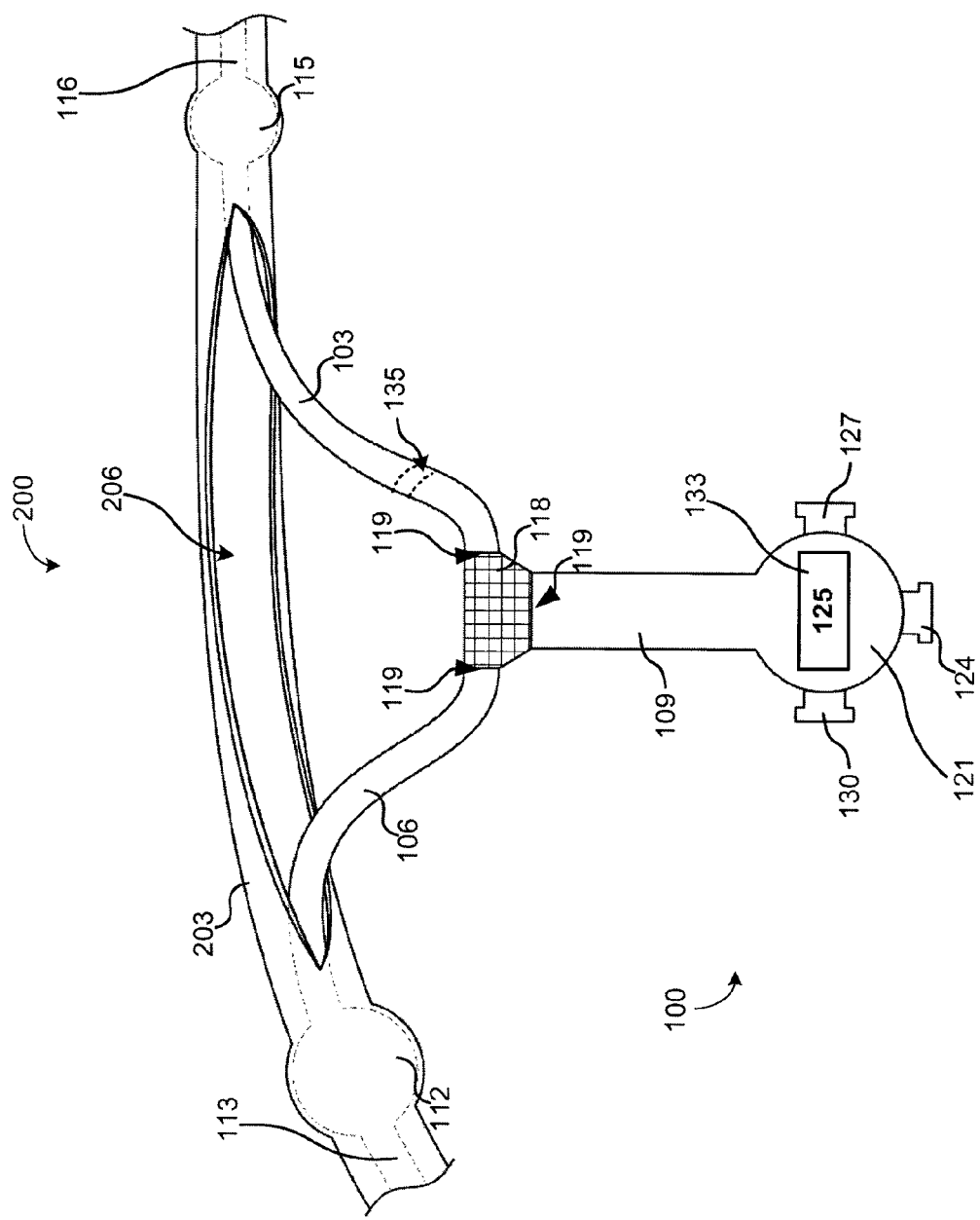
FIG. 2 is a diagram illustrating an example arterial shunt in use within an artery in accordance with one embodiment of the invention.

Turning now to FIG. 2, a diagram is provided illustrating an example arterial shunt 100 in use within an artery 203. Specifically, the artery 203 is illustrated as having an incision 206 typically made during vascular surgery (e.g., carotid endarterectomy). The incision 206 is of such size as to allow the input end 113 and the output end 116 to be placed into the artery 203. Once the individual ends are in place, balloon elements 112 and 115 are inflated in order to safely secure the ends within the artery, and the shunt 100 is ready to temporarily bypass blood flow around the incision 206.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A medical shunt, comprising:
   a first tubular element having a first connection end and an input end;
   a second tubular element having a second connection end and an output end, the second connection end being connected to the first connection end such that the second tubular element and the first tubular element are in fluid communication;
   an inline filter disposed within the shunt such that the filter removes impurities from fluid flowing from the input end to the output end;
   a flow sensor disposed within the first, second, or third tubular element;
   a first balloon element disposed on the first tubular element near the input end;
   a second balloon element disposed on the second tubular element near the output end;
   a third tubular element having a third connection end and a distal end, the third connection end connected to the first and second connection ends such that the third tubular element is in fluid communication with the first and second tubular elements; and
   a housing connected at the distal end of the third tubular element, the housing comprising:
      a flush port in fluid communication with the first and second tubular elements,
      a flow meter comprising a two-sided digital flow indicator, having a digital meter display on opposing sides of the indicator, in electrical communication with the flow sensor, and
      a balloon inflation port in fluid communication with at least one of the first balloon element or the second balloon element.

2. The shunt of claim 1, wherein the housing further comprises a port for administering medication through the shunt.

3. The shunt of claim 1, wherein the housing further comprises a second balloon inflation port, the second balloon inflation port being in fluid communication with the second balloon element and the balloon inflation port being in fluid communication with the first balloon element.

4. The shunt of claim 1, wherein the flow meter comprises an auditory module.

5. The shunt of claim 4, wherein the auditory module output information relating to blood flow between the input and output ends.

6. The shunt of claim 4, wherein the auditory module emits an audible signal when blood flow between the input and output ends is occluded.

7. The shunt of claim 4, wherein the auditory module is disposed within the housing.

8. The shunt of claim 1, wherein the filter is a heparin-bonded filter.

9. The shunt of claim 1, wherein the filter is disposed inline within the first and second tubular elements.

10. The shunt of claim 9, wherein the filter is located at a junction of the first, second, and third connection ends.

11. The shunt of claim 1, wherein the second tubular element has a smaller gauge than the first tubular element.

12. The shunt of claim 1, wherein the first tubular element has a gauge of 9 or 11 French.

13. The shunt of claim 1, wherein the second tubular element has a gauge of 9 French.

14. The shunt of claim 1, wherein the input and output ends are rounded.

15. The shunt of claim 1, wherein the shunt is self-powered from blood flow.

16. A medical shunt, comprising:
   a first tubular element having a first connection end and an input end;
   a second tubular element having a second connection end and an output end, the second connection end being connected to the first connection end such that the second tubular element and the first tubular element are in fluid communication;
   an inline filter disposed within the shunt such that the filter removes impurities from fluid flowing from the input end to the output end;
   a flow sensor disposed within the first, second, or third tubular element;
   a first balloon element disposed on the first tubular element near the input end;
   a second balloon element disposed on the second tubular element near the output end;
   a third tubular element having a third connection end and a distal end, the third connection end connected to the first and second connection ends such that the third tubular element is in fluid communication with the first and second tubular elements; and
   a housing connected at the distal end of the third tubular element, the housing comprising:
      a flush port in fluid communication with the first and second tubular elements,
      a flow meter comprising a two-sided digital flow indicator, having a digital meter display on opposing sides of the indicator, in electrical communication with the flow sensor,
      a balloon inflation port in fluid communication with at least one of the first balloon element or the second balloon element,
      a port for administering medication through the shunt, and
   a second balloon inflation port, the second balloon inflation port being in fluid communication with the second balloon element and the balloon inflation port being in fluid communication with the first balloon element,
   wherein the shunt is self-powered from blood flow.

17. A medical shunt, comprising:
- a first tubular element having a first connection end and an input end;
- a second tubular element having a second connection end and an output end, the second connection end being connected to the first connection end such that the second tubular element and the first tubular element are in fluid communication, wherein the second tubular element has a smaller or equal gauge than the first tubular element;
- an inline filter disposed within the shunt such that the filter removes impurities from fluid flowing from the input end to the output end;
- a flow sensor disposed within the first, second, or third tubular element;
- a first balloon element disposed on the first tubular element near the input end;
- a second balloon element disposed on the second tubular element near the output end;
- a third tubular element having a third connection end and a distal end, the third connection end connected to the first and second connection ends such that the third tubular element is in fluid communication with the first and second tubular elements; and
- a housing connected at the distal end of the third tubular element, the housing comprising:
  - a flush port in fluid communication with the first and second tubular elements,
  - a flow meter comprising a two-sided digital flow indicator, having a digital meter display on opposing sides of the indicator, in electrical communication with the flow sensor, and
- a balloon inflation port in fluid communication with at least one of the first balloon element or the second balloon element.

18. The shunt of claim 17, wherein the shunt is self-powered from blood flow.

19. The shunt of claim 17, wherein the filter is a heparin-bonded filter.

* * * * *